United States Patent
Harding et al.

(10) Patent No.: US 7,856,083 B2
(45) Date of Patent: Dec. 21, 2010

(54) SYSTEM AND METHOD TO ACCOUNT FOR CROSS-TALK AMONG COHERENT SCATTER DETECTORS

(75) Inventors: Geoffrey Harding, Hamburg (DE); Helmut Rudolf Strecker, Hamburg (DE)

(73) Assignee: Morpho Detection, Inc., Newark, CA (US)

( * ) Notice: Subject to any disclaimer, the term of this patent is extended or adjusted under 35 U.S.C. 154(b) by 1 day.

(21) Appl. No.: 12/263,074

(22) Filed: Oct. 31, 2008

(65) Prior Publication Data

US 2010/0111253 A1 May 6, 2010

(51) Int. Cl.
*G01N 23/20* (2006.01)
(52) U.S. Cl. .......................................... 378/71; 378/86
(58) Field of Classification Search .................. 378/57, 378/70, 71, 86, 87, 124
See application file for complete search history.

(56) References Cited

U.S. PATENT DOCUMENTS

| | | | |
|---|---|---|---|
| 5,642,393 A | 6/1997 | Krug et al. | |
| 6,876,322 B2 | 4/2005 | Keller | |
| 7,283,613 B2 * | 10/2007 | Harding | 378/86 |
| 7,366,282 B2 | 4/2008 | Peschmann | |
| 7,417,440 B2 | 8/2008 | Peschmann et al. | |
| 7,463,720 B2 | 12/2008 | Harding et al. | |
| 2008/0285706 A1 | 11/2008 | Schlomka | |
| 2008/0317311 A1 | 12/2008 | Grass et al. | |

* cited by examiner

*Primary Examiner*—Jurie Yun
(74) *Attorney, Agent, or Firm*—Armstrong Teasdale LLP

(57) ABSTRACT

A method to account for cross-talk among a plurality of coherent scatter detectors of a multi-detector inverse fan beam x-ray diffraction imaging (MD-IFB XDI) system. The MD-IFB XDI system includes a multi-focus x-ray source (MFXS) that emits radiation sequentially from a plurality of focus points denoted by $F_1, F_2, \ldots F_n$ with a running index i. The method includes measuring a diffraction profile $X_k$ for each coherent scatter detector $D_k$ of the plurality of coherent scatter detectors. The diffraction profile includes a spectrum of a number of photons measured in a plurality of corresponding coherent scatter detectors. Each coherent scatter detector $D_k$ is corrected to remove scatter from a plurality of primary beams directed to remaining coherent scatter detectors of the plurality of coherent scatter detectors.

24 Claims, 4 Drawing Sheets

US 7,856,083 B2

SYSTEM AND METHOD TO ACCOUNT FOR CROSS-TALK AMONG COHERENT SCATTER DETECTORS

BACKGROUND OF THE INVENTION

1. Field of the Invention

The embodiments described herein relate to a multi-detector inverse fan beam x-ray diffraction imaging (MD-IFB XDI) system and, more particularly, to a system and method to account for cross-talk among coherent scatter detectors in an MD-IFB XDI system.

2. Description of Prior/Related Art

Known security detection systems are used at travel checkpoints to inspect carry-on and/or checked bags for concealed weapons, narcotics, and/or explosives. At least some known security detection systems include x-ray imaging systems. In an x-ray imaging system, an x-ray source transmits x-rays through a container, for example a suitcase, towards a detector, and the detector output is processed to identify one or more objects and/or one or more materials in the container.

At least some known security detection systems include a multi-detector inverse fan beam x-ray diffraction imaging (MD-IFB XDI) system. MD-IFB XDI systems use an inverse fan-beam geometry (a large source and a small detector) and a multi-focus x-ray source (MFXS). MD-IFB XDI systems also utilize a plurality of detectors to increase an x-ray diffraction imaging (XDI) signal and, thus, reduce measurement time. In addition to the XDI signal, the detectors generate noise including a cross-talk component that increases as the number of employed detectors increases. In at least some known MD-IFB XDI systems, the detectors are positioned along a plane at a maximum distance from neighboring detectors to compensate for cross-talk of scatter from one pencil x-ray beam interfering with a signal of another pencil x-ray beam to the same detector. This limits a total number of detectors that may be utilized and also limits the scatter signal strength that may be achieved with the MD-IFB XDI system.

It is desirable to strip or correct XDI profiles generated during the MD-IFB XDI process to account for the undesirable effects of cross-talk. By stripping or correcting the XDI profiles, a number of employed detectors may be increased to improve the scatter signal-to-noise ratio, which leads to improved detection efficiency and a lower false alarm rate.

BRIEF DESCRIPTION OF THE INVENTION

In one aspect, a method is provided to account for cross-talk among a plurality of coherent scatter detectors of a multi-detector inverse fan beam x-ray diffraction imaging (MD-IFB XDI) system. The MD-IFB XDI system includes a multi-focus x-ray source (MFXS) that emits radiation sequentially from a plurality of focus points denoted by $F_1, F_2, \ldots F_i, \ldots F_n$ with a running index i. The method includes measuring a diffraction profile $X_k$ for each coherent scatter detector $D_k$ of the plurality of coherent scatter detectors. The diffraction profile includes a spectrum of a number of photons measured in a plurality of corresponding coherent scatter detectors. Each coherent scatter detector $D_k$ is corrected to remove scatter from a plurality of primary beams directed to remaining coherent scatter detectors of the plurality of coherent scatter detectors.

In another aspect, a security detection system is provided. The security detection system includes a multi-focus x-ray source (MFXS) configured to emit radiation sequentially from a plurality of focus points denoted $F_1, F_2, \ldots F_i, \ldots F'_n$ with a running index i. A multi-angle primary collimator (MAPC) is configured to select from the radiation emitted at each focus point, a plurality of primary beams, each of which are directed to a corresponding convergence point of a plurality of convergence points labeled $O_1, O_2, \ldots, O_j, \ldots O_m$ with a running index j. A plurality of coherent scatter detectors labeled coherent scatter detectors $D_1, D_2, \ldots D_j, \ldots D_k$ with a running index j are positioned with respect to the corresponding convergence point to record coherent scatter at an angle θ from a primary beam $P_{ij}$ of the plurality of primary beams in coherent scatter detector $D_j$. A processor is coupled in electrical communication with each coherent scatter detector of the plurality of coherent scatter detectors. The processor is configured to account for cross-talk among the plurality of coherent scatter detectors.

BRIEF DESCRIPTION OF THE DRAWINGS

FIG. 1 is a schematic view, in an X-Z plane, of an exemplary security detection system.

FIG. 2 is a schematic view, in an X-Y plane, of the security detection system shown in FIG. 1.

FIG. 3 is a schematic view, in an X-Z plane, of an exemplary x-ray scatter detection system embodied within the security detection system shown in FIGS. 1 and 2.

FIG. 4 is a flowchart of an exemplary method to account for cross-talk among coherent scatter detectors of the security detection system shown in FIGS. 1-3.

DETAILED DESCRIPTION OF THE INVENTION

The embodiments described herein provide a multi-detector inverse fan beam x-ray diffraction imaging (MD-IFB XDI) system configured to emit several pencil x-ray beams from each focus point on a multi-focus x-ray source (MFXS). The MD-IFB XDI system utilizes a plurality of detectors to increase an x-ray diffraction imaging (XDI) signal and, thus, reduce measurement time. The XDI signal includes an undesirable cross-talk component, which increases as the number of detectors employed increases. A stripping or correction procedure described herein by which XDI profiles are stripped or corrected to account for the effects of cross-talk allows utilization of an increased number of detectors in a security detection system, which improves the signal-to-noise ratio leading to an improved detection efficiency and a lower false alarm rate.

A technical effect of the system and method described herein is to account for, such as compensate for, eliminate, or reduce, cross-talk among or between coherent scatter detectors of an MD-IFB XDI system. The MD-IFB XDI system includes an MFXS that emits radiation sequentially from a plurality of focus points denoted by $F_1, F_2, \ldots F_n$ with a running index i. In one embodiment, a diffraction profile, $X_k$, including a spectrum of a number of photons measured in a plurality of corresponding coherent scatter detectors is measured for each coherent scatter detector $D_k$. Each coherent scatter detector $D_k$ is then corrected to remove scatter from a plurality of pencil or primary beams directed to remaining coherent scatter detectors.

While described in terms of detecting contraband including, without limitation, weapons, explosives, and/or narcotics, within checked or carry-on baggage, the embodiments described herein may be used for any suitable security detection or other x-ray diffraction imaging application, including applications in the plastics recycling, pharmaceutical and non-destructive testing industries. Further, angles and/or dimensions shown in the accompanying figures may not be to scale, and may be exaggerated for clarity.

Figure 1:
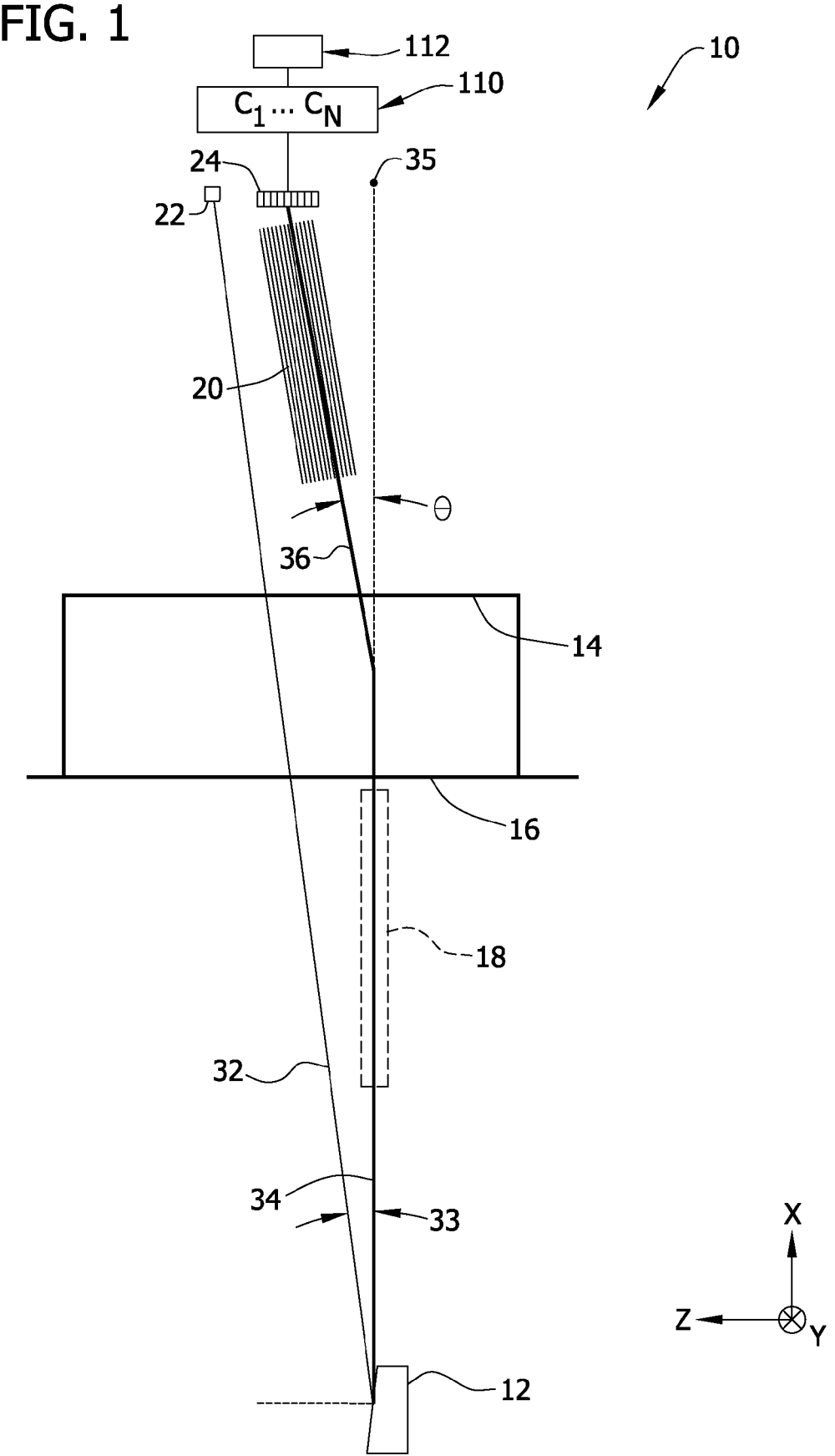
FIGS. 1-4 show exemplary embodiments of the system and method described herein.

FIG. 1 is a schematic view, in an X-Z plane, of an exemplary security detection system 10. In the exemplary embodiment, security detection system 10 is a multi-detector inverse fan beam x-ray diffraction imaging (MD-IFB XDI) system that includes a multi-focus x-ray source (MFXS) 12, an examination area 14, a support 16 configured to support an object, a primary collimator 18, and a secondary collimator 20. Security detection system 10 also includes two types of detectors, an array of transmission detectors 22 and a plurality of discrete coherent x-ray scatter detectors 24. Transmission detectors 22 are offset in a z-axis direction from scatter detectors 24.

In the exemplary embodiment, MFXS 12 is capable of emitting x-ray radiation sequentially from a plurality of focus points, as described below, distributed along MFXS 12 in a direction substantially parallel to a y-axis perpendicular to the z-axis. In the exemplary embodiment, MFXS 12 has approximately 40 focus points. In an alternative embodiment, MFXS 12 has approximately 100 focus points. In further alternative embodiments, MFXS 12 includes any suitable number of focus points that will allow security detection system 10 to function as described herein.

Further, in the exemplary embodiment, MFXS 12 is located on a lower support surface, such as a floor, while transmission detectors 22 and scatter detectors 24 are located on an upper support structure, such as a ceiling. In an alternative embodiment, MFXS 12 is located on an upper support structure, such as a ceiling, while transmission detectors 22 and scatter detectors 24 are located on a lower support surface, such as a floor. Further, in the exemplary embodiment, MFXS 12, transmission detectors 22 and scatter detectors 24 are stationary, support 16 is a conveyor belt capable of movement backward and forward in a direction substantially parallel to the z-axis, and examination area 14 is a baggage tunnel through which the conveyor belt moves. In an alternative embodiment, MFXS 12, transmission detectors 22 and scatter detectors 24 are capable of coordinated movement at least in a direction substantially parallel to the z-axis, and support 16 is stationary. In certain alternative embodiments, MFXS 12, transmission detectors 22, scatter detectors 24 and support 16 are all capable of movement.

In the exemplary embodiment, MFXS 12 is capable of emitting an x-ray fan beam 32 from each focus point of MFXS 12. Each fan beam 32 lies substantially in a plane at an angle 33 relative to a vertical x-axis perpendicular to the z-axis and the y-axis. Each fan beam 32 is directed at transmission detectors 22. In the exemplary embodiment, angle 33 is approximately ten degrees. In an alternative embodiment, angle 33 is approximately fifteen degrees. In further alternative embodiments, angle 33 is any suitable angle that will allow security detection system 10 to function as described herein.

In addition, MFXS 12 is capable of emitting, through primary collimator 18, a set of x-ray pencil beams 34, from each focus point of MFXS 12. Each pencil beam 34 is directed at a corresponding target point 35 which lies in the same X-Y plane as MFXS 12. Further, each target point 35 is positioned at the same X-coordinate value, but at different Y-coordinate values. Because each pencil beam 34 is emitted in the same X-Y plane, only one pencil beam 34 (and only one target point 35) is visible in the X-Z cross-section view of FIG. 1.

A portion of the x-ray radiation from each pencil beam 34 typically is scattered in various directions upon contact with a container (not shown) in examination area 14. Secondary collimator 20 is configured to facilitate ensuring that a portion of scattered radiation 36 arriving at each scatter detector 24 has a constant scatter angle θ with respect to the corresponding pencil beam 34 from which scattered radiation 36 originated. In certain embodiments, scatter angle θ is approximately 0.04 radians. Scatter detectors 24 can be positioned between pencil beams 34 and fan beam 32 to ensure that only scattered radiation from the former and not the latter is detected. For example, secondary collimator 20 is configured to absorb scattered radiation (not shown) that is not parallel to the direction of scattered radiation 36. Further, although, in the exemplary embodiment, secondary collimator 20 and scatter detectors 24 are positioned on one side of pencil beams 34 with respect to the z-axis, in alternative embodiments secondary collimator 20 and scatter detectors 24 may be positioned on the other side, or on both sides, of pencil beams 34 with respect to the z-axis.

In the exemplary embodiment, transmission detectors 22 are charge integration detectors, while scatter detectors 24 are pulse-counting energy-resolving detectors. Transmission detectors 22 and each scatter detector 24 are in electronic communication with a number of channels 110, for example, N number of channels $C_1, \ldots C_N$, wherein N is selected based on the configuration of security detection system 10. Channels 110 electronically communicate data collected by transmission detectors 22 and each scatter detector 24 to a data processing system 112. In the exemplary embodiment, data processing system 112 combines an output from transmission detectors 22 and an output from scatter detectors 24 to generate information about the contents of examination area 14. For example, but not by way of limitation, data processing system 112 may generate multiview projections and/or section images of a container (not shown) in examination area 14 that identify a location in the container of specific materials detected by XDI analysis.

In the exemplary embodiment, data processing system 112 includes a processor 114 in electrical communication with transmission detectors 22 and scatter detectors 24. Processor 114 is configured to receive from scatter detectors 24 output signals representative of the detected x-ray quanta and generate a distribution of momentum transfer values, x, as described below, from a spectrum of energy E of x-ray quanta within scattered radiation detected by scatter detectors 24. As used herein, the term processor is not limited to just those integrated circuits referred to in the art as a processor, but broadly refers to a computer, a microcontroller, a microcomputer, a programmable logic controller, an application specific integrated circuit, and any other suitable programmable circuit. The computer may include a device, such as a floppy disk drive or CD-ROM drive, for reading data from a computer-readable medium, such as a floppy disk, a compact disc-read only memory (CD-ROM), a magneto-optical disk (MOD), or a digital versatile disc (DVD). In alternative embodiments, processor 114 executes instructions stored in firmware.

Figure 2:
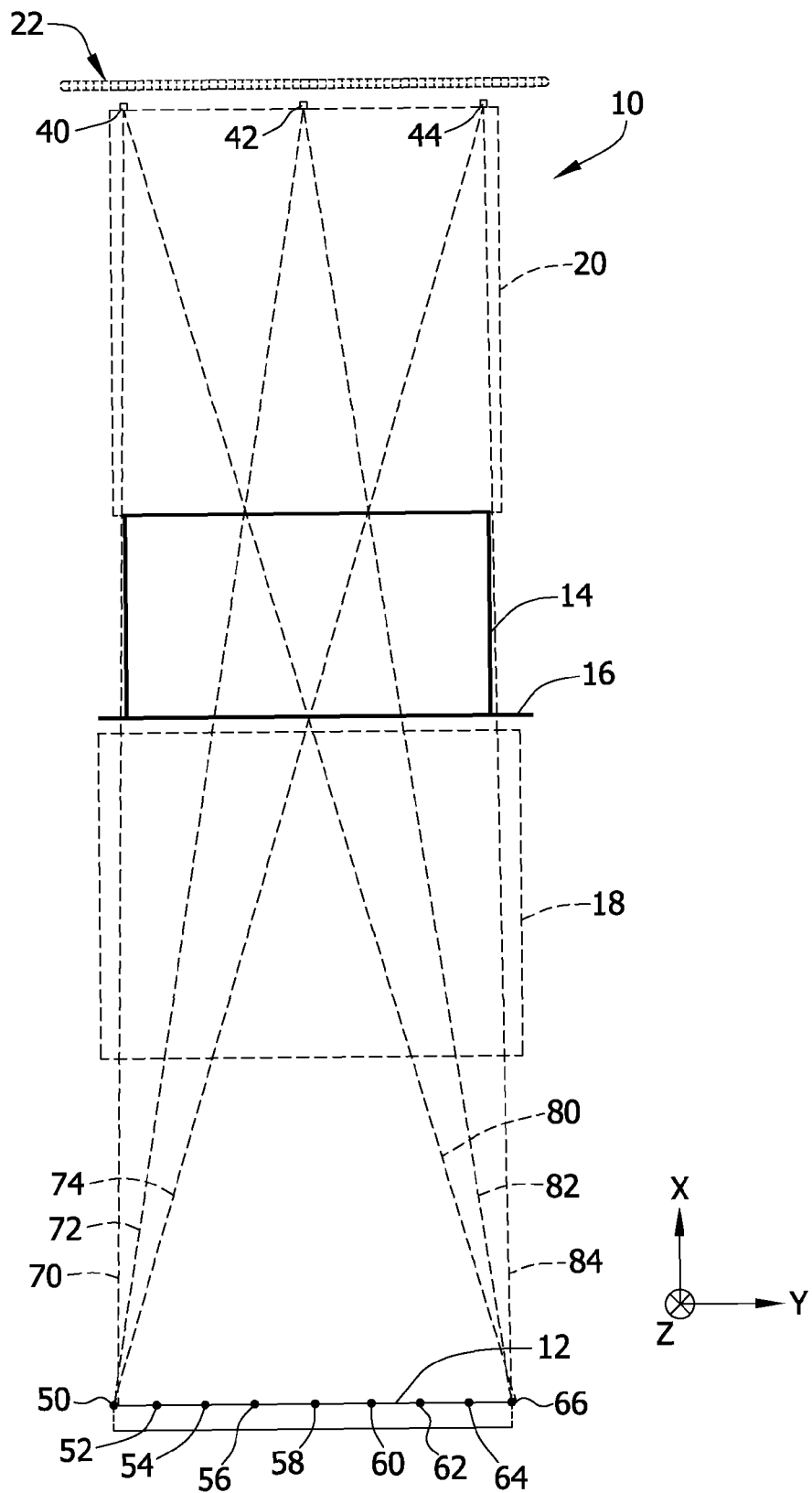

FIG. 2 is a schematic view, in an X-Y plane, of security detection system 10 shown in FIG. 1. With reference to FIGS. 1 and 2, in the exemplary embodiment, scatter detectors 24 include three discrete coherent x-ray scatter detectors 40, 42 and 44. Scatter detectors 40, 42 and 44 share identical x-coordinate values and z-coordinates values and are spaced apart in a direction substantially parallel to the y-axis. Moreover, in the exemplary embodiment, each set of pencil beams 34 generated by MFXS 12 includes three pencil beams corresponding to the number (three) of scatter detectors 40, 42 and 44. In alternative embodiments, a different number of scatter detectors and corresponding different number of pencil beams may be used.

As previously described, MFXS 12 includes a plurality of focus points, of which focus points 50, 52, 54, 56, 58, 60, 62, 64 and 66 are shown in FIG. 2. MFXS 12 is capable of sequentially generating both a fan beam 32 and, through primary collimator 18, a set of pencil beams 34 from each focus point such as focus point 50, 52, 54, 56, 58, 60, 62, 64 and 66. Each pencil beam 34 is targeted at a target point 35 associated with a corresponding scatter detector 40, 42 or 44. For example, the set of pencil beams 34 generated from focus point 50 includes pencil beam 70, pencil beam 72 and pencil beam 74. Scattered radiation 36 having a component with an angle θ in the X-Z plane, shown in FIG. 1, from pencil beam 70 is received by scatter detector 40, scattered radiation 36 from pencil beam 72 is received by scatter detector 42, and scattered radiation 36 from pencil beam 74 is received by scatter detector 44 respectively. For another example, the set of pencil beams 34 generated from focus point 66 includes pencil beam 80, pencil beam 82 and pencil beam 84. Scattered radiation 36 having a component with an angle θ in the X-Z plane, from pencil beam 80 is received by scatter detector 40, scattered radiation 36 from pencil beam 82 is received by scatter detector 42, and scattered radiation 36 from pencil beam 84 is received by scatter detector 44, respectively.

In addition, each fan beam 32 generated sequentially from each focus point of MFXS 12, such as focus point 50, 52, 54, 56, 58, 60, 62, 64 and 66, is targeted at transmission detectors 22. Transmission detectors 22 extend in a direction substantially parallel to the y-axis. Transmission detectors 22 typically receive radiation from each fan beam 32 after fan beam 32 is attenuated by a container (not shown) positioned in examination area 14. In the exemplary embodiment, transmission detectors 22 are dual energy transmission detectors. In certain embodiments, the array of transmission detectors 22 includes approximately 1000 detector elements or modules.

In the exemplary embodiment, security detection system 10 is configured to operate such that focus point 50, the focus point at a first end of MFXS 12 relative to the y-direction, first simultaneously generates both fan beam 32 and a set of pencil beams 34 for which data is collected from transmission detectors 22 and scatter detectors 40, 42 and 44, respectively, and electronically communicated to data processing system 112. Then, focus point 52, the focus point of MFXS 12 adjacent focus point 50 in the y-direction, simultaneously generates both fan beam 32 and a set of pencil beams 34 for which data is collected from transmission detectors 22 and scatter detectors 40, 42 and 44, respectively, and electronically communicated to data processing system 112. The remaining focus points 54, 56, 58, 60, 62, 64 and 66, in sequence along the y-direction, likewise simultaneously generate both fan beam 32 and a set of pencil beams 34 for which data is collected from transmission detectors 22 and scatter detectors 40, 42 and 44, respectively, and electronically communicated to data processing system 112. Security detection system 10 then repeats the sequence starting with focus point 50 again. In certain embodiments, the container under examination (not shown) moves in the z-direction relative to MFXS 12 at a speed that is relatively slow compared to a speed at which MFXS 12 switches among focus points.

In alternative embodiments, the focus points of MFXS 12 generate fan beam 32 and a set of pencil beams 34 in a sequence that is not based upon their relative position along the y-direction. In an exemplary embodiment for checkpoint or "carry-on" luggage screening, the array of transmission detectors 22 has a length parallel to the y-axis of approximately 650 mm, and scatter detectors 24 are spaced sequentially at approximately 250 mm intervals in a direction substantially parallel to the y-axis. Each transmission detector 22 and scatter detector 24 is located approximately 1500 mm from MFXS 12 in a direction substantially parallel to the x-axis. In an exemplary embodiment for checked luggage screening, the array of transmission detectors 22 has a length parallel to the y-axis of approximately 2000 mm, and scatter detectors 24 are spaced sequentially at approximately 50 mm intervals in a direction substantially parallel to the y-axis. Each transmission detector 22 and each scatter detector 24 is located approximately 2000 mm from MFXS 12 in a direction substantially parallel to the x-axis. In alternative embodiments, other suitable dimensions are used that allow all desired portions of examination area 14 to be covered for both XDI analysis and multiview transmission imaging.

Figure 3:
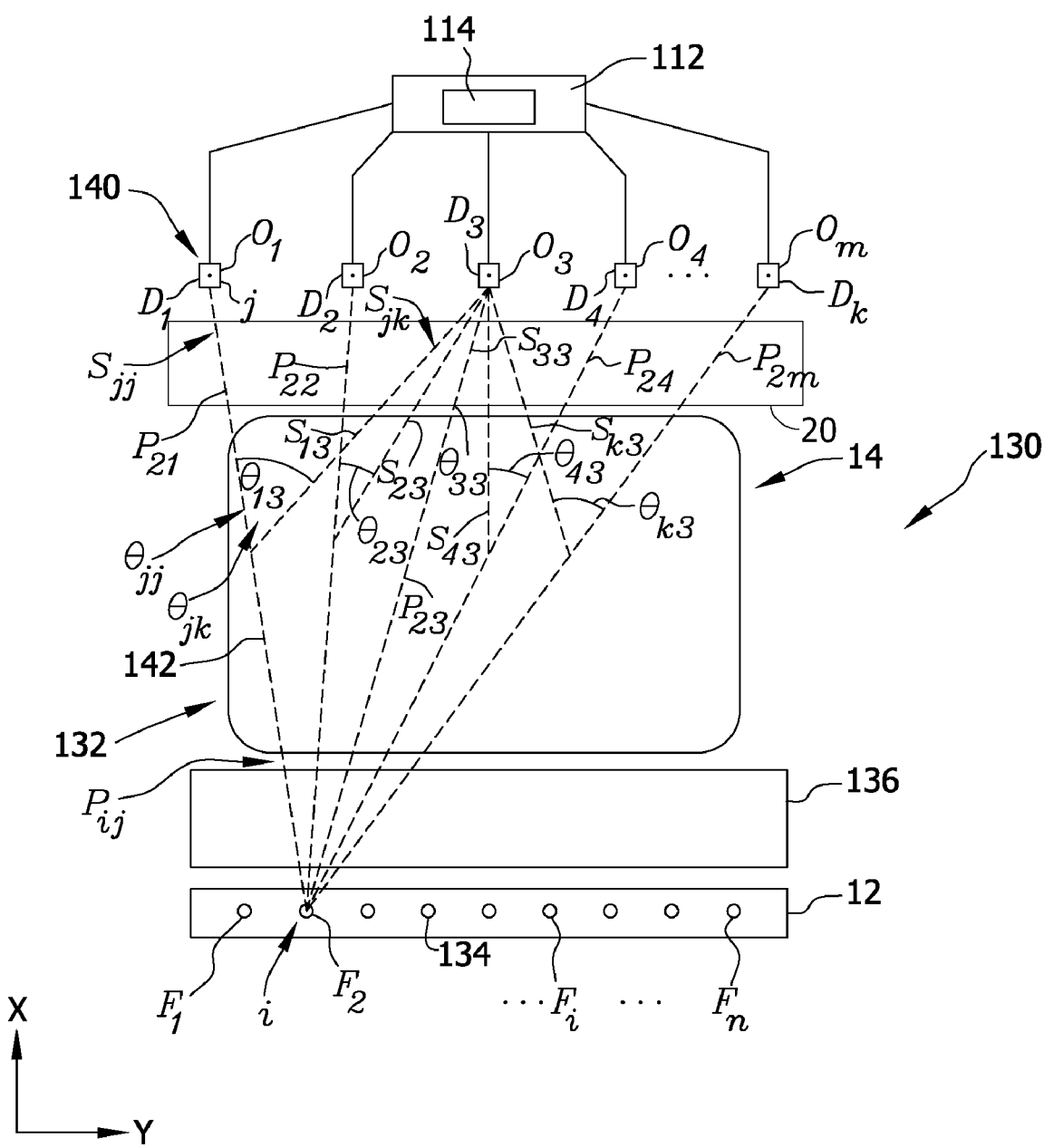

FIG. 3 is a schematic view, in an X-Z plane, of an exemplary x-ray scatter detection system 130 embodied within security detection system 10 shown in FIGS. 1 and 2. Referring further to FIG. 3, in one embodiment, a multi-detector inverse fan beam (MD IFB) 132 is projected along the z-axis. MFXS 12 emits radiation sequentially from a plurality of focus points 134. Focus points 134 are denoted $F_1, F_2, \ldots F_i, \ldots F_n$ with a running index i. A multi-angle primary collimator (MAPC) 136 is configured to select from the radiation emitted at each focus point 134, pencil or primary beams that are directed to a series of convergence points 138 labeled $O_1, O_2, \ldots, O_j, \ldots O_m$ with a running index j. As shown in FIG. 3, each primary beam emitted from each focus point 134 is directed to a corresponding convergence point 138. A plurality of discrete coherent x-ray scatter detectors 140 labeled discrete coherent x-ray scatter detectors $D_1, D_2, \ldots D_j, \ldots D_k$ with a running index j are positioned at a suitable or desirable distance in a direction along the z-axis from a corresponding convergence point 138 to record coherent scatter at an angle θ from primary beam $P_{ij}$ in discrete coherent x-ray scatter detector $D_j$. In one embodiment, this distance is about 30 mm for a scatter angle of about 0.037 radians at a distance of about 750 mm between a scatter center and a corresponding coherent scatter detector $D_j$.

As a primary beam 142 labeled $P_{ij}$ propagates through an object (not shown) positioned within examination area 14, primary beam $P_{ij}$ interacts with the object to produce coherent scatter labeled as a direct scatter beam $S_{jj}$. However, it may occur that coherent scatter from primary beam $P_{ij}$ is detected in neighboring coherent scatter detectors $D_{j+1}$, $D_{j+2}$, $D_{j-1}$ and/or $D_{j-2}$, for example. Such scatter is labeled as a cross-talk scatter beam $S_{jk}$, wherein k=j+1, j+2, j−1, or j−2, for example. Direct scatter beam $S_{jj}$ denotes a scatter beam that originates in primary beam $P_{ij}$ directed to a convergence point j that induces scatter recorded in coherent scatter detector $D_j$ and has a scatter angle $\theta_{jj}$ of approximately 0.04 radians. Cross-talk scatter beam $S_{jk}$ denotes a scatter beam that originates in primary beam $P_{ij}$ directed to convergence point j that induces scatter recorded in coherent scatter detector $D_k$ and has a scatter angle $\theta_{jk}$. Scatter angle $\theta_{jk}$ is greater than scatter angle $\theta_{jj}$ by an amount that depends on a separation distance between coherent scatter detector $D_j$ and coherent scatter detector $D_k$. Considering, for example, a separation distance of approximately 50 millimeters (mm), if $\theta_{jj}$ is approximately 0.04 radians then $\theta_{jk}$ is approximately 0.075 radians.

As shown in FIG. 3, primary beams $P_{21}, P_{22}, P_{23}, P_{24}$, and $P_{2m}$ are emitted from focus point $F_2$ and directed to corresponding convergence points $O_1, O_2, O_3, O_4$, and $O_m$, respectively. As each primary beam $P_{21}, P_{22}, P_{23}, P_{24}$, and $P_{2m}$ moves through examination area 14, each primary beam $P_{21}, P_{22}, P_{23}, P_{24}$, and $P_{2m}$ collides with and/or interacts with an object (not shown) positioned within examination area 14 to produce coherent scatter $S_{13}, S_{23}, S_{33}, S_{43}$, and $S_{k3}$ that is detectable at coherent scatter detector $D_3$, for example. A direct scatter beam $S_{33}$ denotes a scatter beam that originates in primary beam $P_{33}$ directed to convergence point $O_3$ that induces scatter recorded in coherent scatter detector $D_3$ and has a scatter angle $\theta_{33}$ of approximately 0.04 radians. Cross-talk scatter beam $S_{13}$ denotes a scatter beam that originates in primary beam $P_{21}$ directed to convergence point $O_1$ that induces scatter recorded in coherent scatter detector $D_3$ and has a scatter angle $\theta_{13}$. Similarly, cross-talk scatter beam $S_{23}$ denotes a scatter beam that originates in primary beam $P_{22}$ directed to convergence point $O_2$ that induces scatter recorded in coherent scatter detector $D_3$ and has a scatter angle $\theta_{23}$, cross-talk scatter beam $S_{43}$ denotes a scatter beam that originates in primary beam $P_{24}$ directed to convergence point $O_4$ that induces scatter recorded in coherent scatter detector $D_3$ and has a scatter angle $\theta_{43}$, and cross-talk scatter beam $S_{k3}$ denotes a scatter beam that originates in primary beam $P_{2m}$ directed to convergence point $O_m$ that induces scatter recorded in coherent scatter detector $D_3$ and has a scatter angle $\theta_{k3}$. Coherent scatter produced by primary beams interacting with the object may also be detected at coherent scatter detectors $D_1$, $D_2$, $D_4$, and/or $D_k$.

The principle of energy-dispersive XDI is to measure an intensity of x-rays scattered at a constant angle $\theta$ as a function of photon energy level, E. The momentum transfer, x, in this case, where c is a speed of light, h is Planck's constant, and $\theta$ represents constant scatter angles of x-ray quanta of scattered radiation detected by coherent scatter detectors $D_1, D_2, \ldots D_j, D_k$, is:

$$x_k = \frac{E_k}{hc} \cdot \sin\left(\frac{\theta}{2}\right) \qquad \text{Eq. 1}$$

The diffraction profile, $X_k$, measured by coherent scatter detector $D_k$ when focus point $F_i$ is activated is a sum of scatter signals generated by primary beams and scatter beams traveling over a plurality of paths is given by:

$$X_k = \sum_{j=1}^{m} P_{ij} \cdot S_{jk} \qquad \text{Eq. 2}$$

In Equation 2, k denotes a certain coherent scatter detector $D_k$ and j is a running index. The scatter angle $\theta_{jk}$ is a nominal fixed angle of the energy-dispersive XDI arrangement.

Before starting a stripping or correction procedure as described herein, it is necessary to assume that the highest energy region of the diffraction profile, $E_{top}$, corresponding to the highest momentum value, $x_{top}$, is free of cross-talk. The photons of high energy scattered under the large angles $\theta_{ij}$ correspond to a "free atom region" momentum transfer and cannot excite Bragg peaks. The "free atom region" coherent scatter is very faint in comparison with the Bragg peak region and its contribution can be ignored. In conclusion, the coherent scatter cross-talk can be truncated (set to zero) above the highest momentum value, $x_{top}$, and, thus, the measured diffraction profile at the highest photon energy is assumed free from cross-talk contamination. It is hence labeled $X_{jcorr}$. The truncation condition is described by the following equation:

$$X_j(x) = 0 \text{ for } x \geq x_{top} \qquad \text{Eq. 3}$$

This correction procedure only uses values of diffraction profiles from neighboring coherent scatter detectors at higher momentum transfers than the channel being corrected. Thus, it only uses the high-momentum parts of the diffraction profiles that have previously been corrected. It is possible to refine the correction procedure described here. In particular, it is possible to introduce a weighting factor, $W_{ij}$, as indicated in Equation 4. This weighting factor accounts for the effects of obliquity, meaning the reduction in a solid angle that coherent scatter detector $D_k$ presents to scatter beam $S_{jk}$ from primary beam $P_{ij}$ directed at a coherent scatter detector located far away, as well as for an increased attenuation that scatter beam $S_{jk}$ experiences.

$$X_k = \sum_{j=1}^{m} W_{ij} \cdot P_{ij} \cdot S_{jk} \qquad \text{Eq. 4}$$

Fortunately, scatter angle $\theta_{jk}$ increases rapidly with increasing separation between j and k and so the photon energy corresponding to a certain momentum transfer drops rapidly. Hence, it is generally only necessary to correct for contributions from primary beams directed to coherent scatter detector $D_k$ and its immediate neighboring coherent scatter detectors. For these cases, W is approximately unity.

Figure 4:
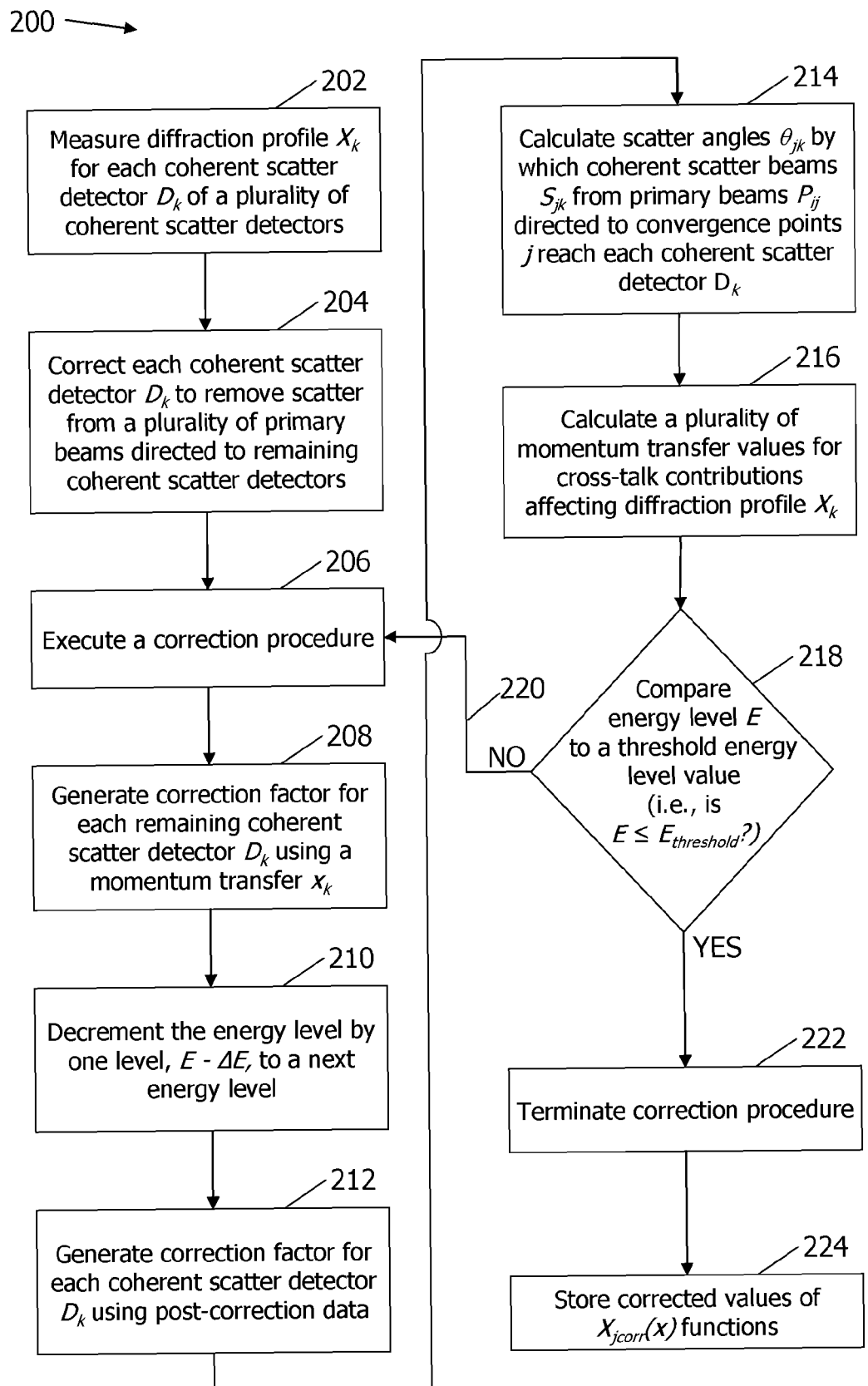

FIG. 4 illustrates an exemplary method 200 to account for cross-talk among or between a plurality of coherent scatter detectors of an MD-IFB XDI system. In this embodiment, the MD-IFB XDI system includes an MFXS that emits radiation sequentially from a plurality of focus points denoted by $F_1, F_2, \ldots F_i, \ldots F_n$ with a running index i. The method includes measuring a diffraction profile $X_k$ for each coherent scatter detector $D_k$ of the plurality of coherent scatter detectors. Diffraction profile $X_k$ includes a spectrum of a number of photons measured in a plurality of corresponding coherent scatter detectors. Each coherent scatter detector $D_k$ is corrected to remove scatter from a plurality of primary beams directed to convergence points of the remaining coherent scatter detectors of the plurality of coherent scatter detectors. A plurality of scatter angles are calculated for each focus point of the plurality of focus points by which scatter from primary beams directed to convergence points for the remaining coherent scatter detectors reaches each coherent scatter detector $D_k$.

Referring to FIG. 4, method 200 includes measuring 202 a diffraction profile $X_k$ for each coherent scatter detector $D_k$ of the plurality of coherent scatter detectors. The diffraction profile $X_k$ includes a spectrum of a number of photons measured in a plurality of corresponding coherent scatter detectors. Each coherent scatter detector $D_k$ is corrected 204 to remove scatter from a plurality of primary beams directed to remaining coherent scatter detectors of the plurality of coherent scatter detectors. In one embodiment, a plurality of scatter angles is calculated for each focus point by which scatter, such as scatter beams, from primary beams directed to convergence points for the remaining coherent scatter detectors reaches each coherent scatter detector $D_k$. For example, referring again to FIG. 3, scatter angles $\theta_{13}$, $\theta_{23}$, $\theta_{33}$, $\theta_{43}$, and $\theta_{k3}$ are calculated for focus point $F_2$ by which scatter beams $S_{13}$, $S_{23}$, $S_{33}$, $S_{43}$, and $S_{k3}$ from primary beams $P_{21}$, $P_{22}$, $P_{23}$, $P_{24}$, and $P_{2m}$ directed to corresponding convergence points $O_1$, $O_2$, $O_3$, $O_4$, and $O_m$, respectively, reach coherent scatter detector $D_3$. Similarly, scatter angles may also be calculated for scatter beams from primary beams directed to corresponding convergence points that reach the remaining coherent scatter detectors $D_1$, $D_2$, $D_4$, and/or $D_k$.

Each coherent scatter detector $D_k$ is corrected 204 by executing 206 a correction procedure assuming that a highest photon energy value, $E_{top}$, of diffraction profile, $X_k$, corresponding to a highest momentum transfer value, $x_{top}$, is free of cross-talk. In one embodiment, method 200 begins with initializing variables starting at a highest momentum value, $x_{top}$, (corresponding to the highest photon energy value $E_{top}$) of diffraction profile, $X_1$, recorded by a first coherent scatter detector $D_1$ irradiated by a primary beam $P_{11}$ from a first focus point $F_1$. During execution 206 of the correction procedure, a coherent scatter cross-talk above highest momentum transfer value, $x_{top}$, is truncated such that a measured diffraction profile, $X_k$, at highest photon energy value, $E_{top}$, is free from cross-talk contamination. The measured diffraction profile, $X_k$, is labeled as $X_{jcorr}$, pursuant to the truncation condition described by Equation 3. A correction factor is generated 208 for each of the remaining coherent scatter detectors using a momentum transfer, $x_k$, as set forth in Equation 1. An energy level, E, is decremented 210 by one level, E−ΔE, to a next energy level and a correction factor is generated 212 for each coherent scatter detector $D_k$ using post-correction data. In one embodiment, if a momentum transfer value is greater than a highest momentum transfer value, $x_{top}$, $X_{jcorr}$ it set to zero.

A plurality of scatter angles $\theta_{jk}$ are calculated 214 by which the plurality of coherent scatter beams $S_{jk}$ from the plurality of primary beams $P_{ij}$ directed to a plurality of convergence points j reaches each coherent scatter detector $D_k$. A plurality of momentum transfer values are then calculated 216 for cross-talk contributions affecting the diffraction profile, $X_k$. Using Equation 1, momentum transfer values for cross-talk contributions from Equation 2 (looping over j) affecting diffraction profile, $X_k$, are calculated. If the momentum transfer is higher than $x_{top}$, the truncation condition set forth in Equation 3 is used to set $X_{jcorr}$ to zero. Known values of the corrected diffraction profile, $X_{jcorr}$, are subtracted from known values of the coherent scatter detector under consideration, $X_{kcorr}$. This procedure is completed to loop over all values of k and i and then repeated to loop over energy levels, E. An energy level, E, is compared 218 to a threshold energy level value, $E_{threshold}$. If the energy level, E, is not lowered to below the threshold energy level value, $E_{threshold}$, correction procedure is repeated 220. When the energy level, E, is lowered by decrementing E to below the threshold energy level value, such as 30 keV, i.e., $E \leq E_{threshold}$, the procedure is terminated 222 and the corrected values of $X_{jcorr}(x)$ functions are stored 224.

The above correction procedure accounts for coherent scatter and single Compton scatter, both of which are functions of x, but not for multiple scatter. This is not a serious issue in the security screening application, where the concern is mainly to determine Bragg peak positions. The peak positions are not falsified to an appreciable degree by a smoothly-varying multiple scatter background. It is quite possible to space coherent scatter detectors about 40 mm apart such that 25 coherent scatter detectors can be utilized to scan a suitcase, for example, having a width of about 1000 mm.

The method and system described herein provide for stripping or correcting XDI diffraction profiles to account for the effects of cross-talk. This correction procedure increases the number of coherent scatter detectors that may be applied to improve the scatter signal-to-noise ratio leading to improved detection efficiency and lower false alarm rate. This correction procedure can be incorporated with an MD-IFB XDI technique in which several pencil x-ray beams leave each focus point on an MFXS. Each pencil x-ray beam is directed to a corresponding convergence point in the coherent scatter detector plane to limit the cross-talk of scatter from one pencil x-ray beam infecting or interfering with a signal of another pencil x-ray beam to the same coherent scatter detector such that a distance between neighboring coherent scatter detectors can be reduced, whereby the total number of coherent scatter detectors that may be used is increased. The stripping or correction procedure removes cross-talk that allows the use of a greater number of coherent scatter detectors in the MD-IFB XDI system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method to account for cross-talk among a plurality of coherent scatter detectors of a multi-detector inverse fan beam x-ray diffraction imaging (MD-IFB XDI) system, said method comprising:

emitting a plurality of primary beams simultaneously from an x-ray source, each primary beam of the plurality of primary beams is directed to a corresponding convergence point associated with a corresponding coherent scatter detector of the plurality of coherent scatter detectors, each primary beam is configured to interact with an object to produce a scatter radiation;

measuring a diffraction profile $X_k$ at each coherent scatter detector $D_k$ of the plurality of coherent scatter detectors, each diffraction profile $X_k$ comprises a spectrum of a number of photons from the scatter radiation measured by the coherent scatter detector $D_k$, wherein each diffraction $X_k$ includes a cross-talk component arising from at least the primary beam directed to the convergence point associated with at least a second of the plurality of coherent scatter detectors $D_j$;

generating, for each of a plurality of energy levels within the spectrum measured in the diffraction profile $X_k$, a correction factor for the cross-talk component based on the energy level and a scatter angle defined between the primary beam directed to the convergence point associated with the coherent scatter detector $D_j$ and a scatter radiation path from that primary beam to the coherent scatter detector $D_k$; and correcting each diffraction profile $X_k$ corresponding to each coherent scatter detector $D_k$ to remove the cross-talk component.

2. A method in accordance with claim 1, further comprising calculating a plurality of scatter angles by which scatter beams arising from primary beams directed to convergence points for the remaining coherent scatter detectors reaches each coherent scatter detector $D_k$.

3. A method in accordance with claim 1, further comprising assuming that above a highest energy value, $E_{top}$, of the spectrum measured in the diffraction profile $X_k$ corresponding to a highest momentum transfer value, $x_{top}$, the cross-talk component is zero.

4. A method in accordance with claim 3, comprising wherein said generating a correction factor comprises using a momentum transfer $x_k$, wherein:

$$x_k = \frac{E_k}{hc} \cdot \sin\left(\frac{\theta}{2}\right)$$

wherein $E_k$ is the energy level, h is Planck's constant, c is the speed of light and $\theta$ is the scatter angle defined between the primary beam directed to the convergence point associated with the coherent scatter detector $D_j$ and a scatter radiation path from that primary beam to the coherent scatter detector $D_k$.

5. A method in accordance with claim 3, wherein said generating a correction factor for each of a plurality of energy levels comprises starting at the energy level designated by $E_{top}$ and successively decrementing the energy level to a next energy level, thereby generating a correction factor at each of the plurality of energy levels for each coherent scatter detector $D_k$ using post-correction data from a higher energy level.

6. A method in accordance with claim 5, further comprising:
setting the correction factor to zero if the momentum transfer $x_k$ is greater than or equal to $x_{top}$; and
setting the correction factor to the value of the diffraction profile measured at the coherent scatter detector $D_j$ evaluated at the momentum transfer value $x_k$ if the momentum transfer $x_k$ is less than or equal to $x_{top}$.

7. A method in accordance with claim 6, wherein said correcting each diffraction profile $X_k$ comprises subtracting the correction factor from the value of the diffraction profile $X_k$ evaluated at the momentum transfer value $x_k$.

8. A method in accordance with claim 5, further comprising terminating the correction procedure when the energy level is decremented below a threshold value.

9. A method in accordance with claim 3, wherein
the x-ray source comprises a multi-focus x-ray source (MFXS) configured to emit radiation sequentially from a plurality of focus points denoted by $F_1, F_2, \ldots F_n$ with a running index i, said method further comprising:
activating each focus point $F_i$ in a sequence, each activated focus point $F_i$ emits the plurality of primary beams; and
measuring a diffraction profile $X_k$ at each coherent scatter detector $D_k$ of the plurality of coherent scatter detectors while each focus point $F_i$ is activated, wherein said generating a correction factor for each of a plurality of energy levels further comprises looping through of the plurality of focus points.

10. A method in accordance with claim 3, further comprising:
initializing the correction factor to zero at the momentum transfer value, $x_{top}$, corresponding to the highest energy value, $E_{top}$, of the spectrum measured in the diffraction Profile $X_k$.

11. A method in accordance with claim 1, said at least second coherent scatter detector $D_j$ comprises multiple coherent scatter detectors $D_j$ with a running index and said generating a correction factor for each of a plurality of energy levels further comprises looping through each scatter detector $D_j$ for each energy level.

12. A method in accordance with claim 1, wherein
said generating a correction factor further comprises the use of a weighting factor defined for the scatter radiation path from the primary beam directed to the convergence point associated with the coherent scatter detector $D_j$ to the coherent scatter detector $D_k$.

13. A method in accordance with claim 12, wherein the weighting factor
accounts for at least one of (i) a reduction in solid angle that the coherent scatter detector $D_k$ presents to the scatter radiation path and (ii) an increased attenuation associated with the scatter path.

14. A security detection system, comprising:
an x-ray source configured to emit radiation;
a multi-angle primary collimator configured to select from the radiation emitted a plurality of primary beams each directed to a corresponding convergence point of a plurality of convergence points, each primary beam is configured to interact with an object to produce a scatter radiation;
a plurality of coherent scatter detectors each associated with a corresponding one of the plurality of convergence points and each configured to measure a number and an energy of photons from the scatter radiation; and
a processor coupled in electrical communication with each said coherent scatter detector of the plurality of coherent scatter detectors, said processor configured to:
record a diffraction profile $X_k$ at each said coherent scatter detector $D_k$ of said plurality of coherent scatter detectors, each diffraction profile $X_k$ comprises a spectrum of the number of photons from the scatter radiation measured by said coherent scatter detector $D_k$, wherein each diffraction profile $X_k$ includes a cross-talk component arising from at least the primary beam directed to the convergence point associated with at least a second of said plurality of coherent scatter detectors $D_j$;
generate, for each of a plurality of energy levels within the spectrum measured in the diffraction profile $X_k$, a correction factor for the cross-talk component based on the energy level and a scatter angle defined between the primary beam directed to the convergence point associated with said coherent scatter detector $D_j$ and a scatter radiation path from that primary beam to said coherent scatter detector $D_k$; and
correct each diffraction profile $X_k$ corresponding to each coherent scatter detector $D_k$ to remove the cross-talk component.

15. A security detection system in accordance with claim 14, wherein said x-ray source comprises a multi-focus x-ray source (MFXS) configured to emit radiation sequentially from a plurality of focus points denoted by $F_1, F_2, \ldots F_n$ with a running index i, and said processor is further configured to:
activate each said focus point $F_i$ in a sequence, wherein said multi-angle primary collimator is configured to select from the radiation emitted the plurality of primary beams from said activated focus and
record a diffraction profile $X_k$ at each said coherent scatter detector $D_k$ of said plurality of coherent scatter detectors while each said focus point $F_i$ is activated; and
loop through each diffraction profile $X_k$ for each of the plurality of focus points when generating a correction factor for each of the plurality of energy levels.

16. A security detection system in accordance with claim 15, wherein said at least second coherent scatter detector $D_j$ comprises multiple coherent scatter detectors $D_j$ with a running index j, and said processor is further configured to loop through each scatter detector $D_j$ for each energy level.

17. A security detection system in accordance with claim 14, wherein said processor is further configured to assume that above a highest energy value $E_{top}$ of the spectrum measured in the diffraction profile $X_k$ corresponding to a highest momentum transfer value $x_{top}$ the cross-talk component is zero.

18. A security detection system in accordance with claim 17, wherein the correction factor is generated using a momentum transfer $x_k$, wherein:

$$x_k = \frac{E_k}{hc} \cdot \sin\left(\frac{\theta}{2}\right)$$

wherein $E_k$ is the energy level, h is Planck's constant, c is the speed of light and θ is the scatter angle defined between the primary beam directed to the convergence point associated with the coherent scatter detector $D_j$ and a scatter radiation path from that primary beam to the coherent scatter detector $D_k$.

19. A security detection system in accordance with claim 18, wherein the correction factor for each of the plurality of energy levels is generated by starting at the energy level designated by $E_{top}$ and successively decrementing the energy level to a next energy level, thereby generating a correction factor for each said coherent scatter detector $D_k$ using post-correction data.

20. A security detection system in accordance with claim 19, wherein said processor is further configured to:
set the correction factor to zero if the momentum transfer $x_k$ is greater than or equal to $x_{top}$; and
set the correction factor to the value of the diffraction profile measured at said coherent scatter detector $D_j$ evaluated at the momentum transfer value $x_k$ if the momentum transfer $x_k$ is less than or equal to $x_{top}$.

21. A security detection system in accordance with claim 19, wherein said processor is further configured to terminate the correction procedure when the energy level is decremented below a threshold energy level value.

22. A security detection system in accordance with claim 18, wherein said processor is further configured to correct each diffraction profile $X_k$ by subtracting the correction factor from the value of the diffraction profile $X_k$ evaluated at the momentum transfer value $x_k$.

23. A security detection system in accordance with claim 14, wherein said processor is further configured to use a weighting factor in generating the correction factor, wherein the weighting factor is defined for the scatter radiation path from the primary beam directed to the convergence point associated with said coherent scatter detector $D_j$ to said coherent scatter detector $D_k$.

24. A security detection system in accordance with claim 23, wherein the weighting factor accounts for at least one of (i) a reduction in solid angle that said coherent scatter detector $D_k$ presents to the scatter radiation path and (ii) an increased attenuation associated with the scatter path.

* * * * *